United States Patent [19]

Douty

[11] Patent Number: 5,162,568

[45] Date of Patent: Nov. 10, 1992

[54] NITRATION OF ALKANOLS

[75] Inventor: Charles F. Douty, New Castle, Del.

[73] Assignee: E. I. Du Pont de Nemours and Company, Wilmington, Del.

[21] Appl. No.: 180,638

[22] Filed: Apr. 6, 1988

Related U.S. Application Data

[63] Continuation-in-part of Ser. No. 879,512, Jun. 27, 1986, abandoned, which is a continuation-in-part of Ser. No. 792,180, Oct. 28, 1985, abandoned, which is a continuation of Ser. No. 553,567, Nov. 21, 1983, abandoned.

[51] Int. Cl.$^5$ .......................................... C07C 203/04
[52] U.S. Cl. ...................................................... 558/481
[58] Field of Search ................ 260/688; 558/480, 481, 558/483

[56] References Cited

U.S. PATENT DOCUMENTS

| | | | |
|---|---|---|---|
| 2,294,849 | 9/1942 | Olin et al. | 260/467 |
| 2,618,650 | 11/1952 | Hinkamp et al. | 558/480 |
| 2,647,914 | 8/1953 | Allan et al. | 260/467 |
| 2,768,964 | 10/1956 | Spaeth | 260/466 |
| 4,417,903 | 11/1983 | Hinkamp | 260/467 |
| 4,420,311 | 12/1983 | Thomas | 260/466 X |

FOREIGN PATENT DOCUMENTS 2039609  2/1972  Fed. Rep. of Germany.

OTHER PUBLICATIONS

N. N. Lebedev, Chemistry and Technology of Basic Organic and Petrochemical Synthesis, 1981, (English Translation, 1984), pp. 369-371.

Primary Examiner—Deborah L. Kyle
Assistant Examiner—Valerie Fee

[57] ABSTRACT

A process for nitrating alkanols containing 5-13 carbon atoms is disclosed. The nitation takes place at 15°-45° C. using a mixed acid containing 20-30% nitric acid, 55-60% sulfuric acid and 15-20% water, and 2-5%, based on mixed acid, of a stabilizer selected from the class consisting of urea, sulfamic acid and hydrazine.

4 Claims, No Drawings

NITRATION OF ALKANOLS

This is a continuation-in-part of Ser. No. 06/879,512 filed Jun. 27, 1986, now abandoned which is a continuation-in-part of Ser. No. 792,180 filed Oct. 28, 1985 now abandoned; which is a continuation of Ser. No. 553,567, filed Nov. 21, 1983 now abandoned.

BACKGROUND OF THE INVENTION

1. Field of the Invention

The present invention relates to an improved process for preparing nitrates, such as ethylhexyl nitrate, from alcohols, such as ethylhexyl alcohol, using mixed nitric acid and sulfuric acid stabilized with urea, hydrazine or sulfamic acid.

2. Background of the Invention

The prior art disclosed using urea, sulfamic acid or hydrazine at temperatures above about 50°–60° C. when the nitrating acid concentration of the sulfuric-nitric acid-water mixture is low. Nitrating acid concentration, which influences reaction kinetics, is defined at the start of the reaction by the formula $$C_{H_2SO_4} \frac{100}{100 - C_{HNO_3}},$$

where $C_{H_2SO_4}$ and $C_{HNO_3}$ are, respectively, the concentrations of sulfuric acid and nitric acid in the sulfuric-nitric acid-water mixture. At the end of the reaction it is defined by the formula $$C_{H_2SO_4} \frac{100}{100 - C_{HNO_3} + \frac{18}{63} C_{HNO_3}}$$

See N. N. Lebedev, *Chemistry and Technology of Basic Organic and Petrochemical Synthesis*, MIR Publishers, Moscow, USSR, 1981 (English Translation, 1984). U.S. Pat. No. 2,768,964 teaches the low nitrating acid concentration reaction. That patent discloses nitrating alcohols using, by weight, 15–50% sulfuric acid, 10–30% nitric acid, 30–50% water and at least 1% urea, sulfamic acid or hydrazine, the reaction mixture being maintained at 65°–110° C. until the alkyl nitrate formed is separated therefrom. The initial nitrating acid concentration in U.S. Pat. No. 2,768,964 ranges from 23 to 62.5 weight % and the final concentration ranges from 20 to 60 weight %.

The art also teaches use of stabilizing agents such as urea or sulfamic acid at high nitrating acid concentrations but only at temperatures below 0° C. The German Offenlegungsschrift (OLS) 2,039,609 discloses nitrating glycol ethers at −15° to 0° C. with 0.8 to 1.5 moles of nitric acid and 1.5 to 4.0 moles of sulfuric acid per mole of alcohol. The water content is not specified, but from the examples in OLS 2,039,609, the initial nitrating acid concentration can be calculated to range from about 83 to 89 weight % and the final from about 78 to 82 weight %. Urea or sulfamic acid at concentration of about 0.2 to 2 weight % of the alcohol is used. OLS 2,038,609 emphasizes that dangerous oxidation and side reactions are suppressed by working with the sulfuric and nitric acids within the above ranges at temperatures in the −15° to 0° C. range.

It is well known in the art that urea reacts with the acids involved in the reaction. When the nitrating acid concentration and temperatures are increased, the rate of reaction with urea increases dramatically. Thus, at the high nitrating acid concentrations of OLS 2,039,609 and the temperature range above that set forth in that publication, the urea would be expected to react so quickly with the acid that the urea would be depleted and the temperature would rise so quickly that the reaction of the glycol ether with the acid could not be controlled in plant operation.

U.S. Pat. No. 2,618,650 disclosed nitrating alcohols with mixed sulfuric-nitric acid containing 60–68% sulfuric acid, 20–30% nitric acid and 7–14% water at 0° to 20° C. The calculated initial nitrating acid concentration ranges from about 81 to 91 weight % with the final from about 74 to 83 weight %. Consistent with the teachings of OLS 2,039,609, a stabilizing agent such as urea or sulfamic acid is not used at the 0°–20° C. temperature.

U.S. Pat. No. 2,294,849 disclosed manufacture of nitrate esters of aliphatic alcohols at reduced pressures using nitric acid and a small quantity of urea to inhibit oxidation.

When nitric acid reacts with an alkanol to form a nitrate, it does so reversibly and with a relatively small amount of heat generated (about 7 Kcal/mole of alkanol). When nitrous acid is present, it catalyses the oxidation of the alkanol by the nitric acid, an irreversible reaction that also produces more nitrous acid (autocatalytic) and that generates a high amount of heat (120 to 1,000 Kcal/mole). The heat generated depends on the amount of alkanol added to the reaction (At 50% of stoichiometric, about 480 Kcal/mole; and at about 12.5% for an octal alcohol, about 1,000 Kcal/mole).

Urea also reacts with nitric acid generating about 65 to 87 Kcal/mole depending on the strength of the nitrating acid.

It is important to avoid excessive heat generation from a commercial standpoint to minimize energy requirements (cooling or heating especially over long periods of time) and to assure safe operation (a paramount consideration in the operation of a nitrating plant). Therefore, it is essential to completely eliminate nitrous acid that is normally present with nitric acid prior to the addition of the alkanol and to remove nitrous acid as it is formed during the reaction and before it can autocatalyze. While it is known that a stabilizing compound such as urea reacts about 10 times faster with nitrous than with nitric acid and can therefore be used to eliminate the nitrous acid, the amount of stabilizer must be minimized due to its heat contribution.

Reaction rates for all the reactions depend on nitrating acid concentration and temperature. To be commercially important, the principle reaction of nitric acid with the alkanol to form nitrate should be essentially complete in less than about 8 hours. Higher nitrating acid concentrations permit running at lower temperature while lower concentrations require higher temperature to complete the principles reaction in the desired time. Safety (margin of safety), however, also depends on nitrating acid concentration and temperature since at higher nitrating acid concentrations and temperature, the stabilizing agent reacts faster generating more heat and, when dissipated, autocatalytic nitrous acid oxidation will become the principle reaction fueled by unreacted alkanol as well as alkanol generated by hydrolysis of the alkanol nitrate. Simply adding more stabilizing agent at this time will only increase the heat and cause further safety problems.

For example, when nitrating 2-ethylhexanol at the 83% nitrating acid concentration of OLS 2,039,609, the reaction would be essentially complete in about 2 hours at about 10° C. While this reaction time would be acceptable, the margin of safety would be unacceptable because failure of cooling or agitation would quickly result in an uncontrollable exotherm as urea would quickly be dissipated and the nitrous acid would not be removed before autocatalysis.

On the other hand, at the 62.5% of U.S. Pat. No. 2,768,964, the reaction would be essentially complete in an unacceptably long time of about 15 hours at about 45° C. But, since all reactions are slow in this case and the available cooling would be greater (a higher temperature difference between the cooling media and the reactants), the safety margin would be great.

The preferred operating temperature is ambient temperature because of the following:

1. cooling with brine or heating is not required, thereby providing a lower cost of operation;
2. the temperature difference between the coolant, particularly in the case of brine, is greater providing a greater margin of safety;
3. less unreacted urea and alakanol is present at ambient temperature than at lower temperatures providing less fuel in the event of a cooling or agitation failure; and
4. lower nitrating acid concentration results in less heat generation with acceptable reaction rates than with the higher concentrations required at lower temperatures.

The present invention provides a safe mixed sulfuric-nitric acid process that has the advantages of being able to operate with concentrated nitrating acid at temperatures between 15° C. and 45° C. without causing rapid depletion of urea and resulting in unsafe operating conditions. Further it avoids the cost penalties of the refrigeration required to operate at sub-zero degree centigrade temperatures for highly concentrated nitrating acid with urea. It also avoids the need and cost for heating to temperatures greater than 50° to 60° C. or operating at reduced pressures for low concentrations with urea.

SUMMARY OF THE INVENTION

The present invention relates to a process of nitrating alcohols using a mixed acid containing 20-30% nitric acid, 55-60% sulfuric acid and 15-20% water to which is added 2-5% by weight, based on mixed acid, of urea, sulfamic acid or hydrazine at 0°-50° C. After nitration, the acid and alkyl nitrate are separated by decantation and the alkyl nitrate washed with water and neutralized.

DETAILED DESCRIPTION

In carrying out the process of the present invention a reactor is charged with a mixed acid comprising 20-30% by weight nitric acid, 55-60% by weight sulfuric acid and 15-20% by weight water. The mixed acid is agitated and the temperature adjusted to 15°-45° C. with 22°-28° C. being the preferred range.

From 2-5% by weight, based on the mixed acid, of a stabilizer selected from the group consisting of urea, sulfamic acid and hydrazine are then gradually added to the mixed acid over a period of 15 minutes to 1 hour. During stabilizer addition, the temperature tends to rise but it should still be maintained within the range of 0°-50° C. with from 30°-35° C. being the preferred range.

The alcohol is then added to the reaction mixture over a period of ½-3 hours. Generally the alcohol will be a primary monohydric alkanol containing from 5-13 carbon atoms, with 2-ethylhexyl alcohol being preferred. After adding the alcohol, the reaction medium is held at 0°-50° C., with 30°-35° C. being preferred for ½-3 hours. Then the agitation is stopped and the reaction medium allowed to separate into a top layer comprising alkyl nitrate and a bottom layer comprising mixed acid. The bottom layer is drained and the remaining alkyl nitrate is repeated washed by agitating it with a dilute aqueous basic salt solution each of which is removed as a separate layer after agitation is stopped.

In the Example all parts are by weight.

EXAMPLE

A reactor is charged with 13.48 parts of mixed acid containing 3.33 parts $HNO_3$, 7.77 parts $H_2SO_4$ and 2.38 parts $H_2O$. The mixed acid is agitated and its temperature adjusted to 25°±3° C. Urea (0.40 part) is added to the mixed acid over a period of ½ hour and the temperature allowed to rise to 32.5°±2.5° C. 2-Ethylhexyl alcohol (5.85 parts) are added to the reactor at a rate of 0.065 part per minute while maintaining the temperature at 32.5°±2.5° C. After addition of 2-ethylhexyl alcohol, the reaction mixture is held at 32.5°±2.5° C. for 1 hour at which time agitation is stopped and the bottom acid layer which forms is drained from the reactor. An aqueous 10% sodium sulfate solution (2.73 parts) is added to the reactor and the resulting mixture agitated. After 15 minutes, agitation is stopped and the bottom aqueous solution layer, which forms, is separated. An aqueous 10% sodium sulfate solution is added to the ethylhexyl nitrate layer which is agitated for 15 minutes at which point 0.50 part of an aqueous 10% sodium carbonate solution is slowly added. An additional 2.73 parts of a 10% aqueous sodium sulfate solution is added to the reactor and agitated for 15 minutes, after which the lower aqueous layer is drained. Another 2.73 parts of 10% aqueous sodium sulfate solution is added to the reactor and the contents agitated for 15 minutes after which 0.50 part 10% aqueous sodium carbonate is added, the agitation stopped and the lower aqueous layer drained. The 2-ethylhexyl nitrate product is obtained in 97% yield, i.e., 7.64 parts.

I claim:

1. A process for making an alkyl nitrate comprising the following steps:
   a. preparing a mixed acid containing 20-30 weight percent nitric acid, 55-60 weight percent sulfuric acid and 15-20 weight percent water;
   b. adjusting temperature of the mixed acid to 15°-45° C.;
   c. adding 2-5 weight percent, based on mixed acid, of a stabilizer selected from the class consisting of urea, sulfamic acid and hydrazine while maintaining the temperature at 15°-45° C.; and
   d. then mixing an alkanol containing 5-13 carbon atoms into the mixed acid and stabilizer and carrying out a reaction at 15°-45° C.

2. The process of claim 1 wherein the stabilizer is urea.

3. The process of claim 2 wherein the alkanol is 2-ethylhexyl alcohol.

4. The process of claim 3 wherein the reaction is carried out at from about 30° C. to about 35° C.

* * * * *